United States Patent [19]

Michielli et al.

[11] Patent Number: 5,766,178

[45] Date of Patent: Jun. 16, 1998

[54] BONE PLUG

[75] Inventors: Michael Michielli, Hoboken, N.J.; Roger N. Levy, Pound Ridge, N.Y.

[73] Assignee: Howmedia Inc., New York, N.Y.

[21] Appl. No.: 766,640

[22] Filed: Dec. 13, 1996

[51] Int. Cl.$^6$ .................................. A61B 17/56
[52] U.S. Cl. ............................................. 606/95
[58] Field of Search ...................... 606/95, 92, 93, 606/94, 62, 63, 64, 86

[56] References Cited

U.S. PATENT DOCUMENTS

| | | | |
|---|---|---|---|
| 4,245,359 | 1/1981 | Stuhmer | 606/95 |
| 4,302,855 | 12/1981 | Swanson | |
| 5,078,746 | 1/1992 | Garner | 623/16 |
| 5,376,120 | 12/1994 | Sarver et al. | 623/16 |
| 5,383,932 | 1/1995 | Wilson et al. | 623/16 |

FOREIGN PATENT DOCUMENTS 2052267  1/1981  United Kingdom ............... 606/95

OTHER PUBLICATIONS

Richards' pamphlet—"Buck™ Cement Restrictor", 1981.
Dow Corning Wright advertisement, "Silastic®Bone Plug Implant" 1980.
Richards' Catalog page, "Bechtol Total Hip System", 1977.

Primary Examiner—Guy V. Tucker
Attorney, Agent, or Firm—Peter C. Richardson; Lawrence C. Akers; Raymond W. Augustin

[57] ABSTRACT

The plug is made of a plastic material and acts as a cement barrier for openings produced by an operative procedure in medullated bones. The plug is clamped between the side walls of the opening of the bone by means of elastic flanges and prevents the bone cement from escaping downwards on insertion of an intramedullary stem or upon pressurization of the bone cement.

8 Claims, 2 Drawing Sheets

BONE PLUG

BACKGROUND OF THE INVENTION

1. Field of the Invention

This invention relates to a plug for insertion in the medullary canal of a bone. More particularly, this invention relates to a plug for insertion into a bone in which an intramedullary stem of an endoprosthesis is to be anchored by means of bone cement.

2. Description of the Prior Art

As is known, when an endoprosthesis is to be anchored in a bone by means of a bone cement, the cement is first introduced into an operatively prepared opening in the bone and then when the cement has turned to a pasty consistency, a stem of the prosthesis is pressed or knocked into the pasty substance. However, a difficulty which may arise during this process because the bone cement which is present in the opening and which should be displaced as far as possible against the side walls of the opening and along the stem axis, is, instead, pressed further into the bone in the axial direction of the stem or opening.

Hip replacement surgery in a common remedy for many different hip diseases where the hip joint is deteriorated. A common technique for restoring the joint is placing a prosthesis in the proximal femur and fixing it to the bone with bone cement.

In cemented hip surgery, it is a common practice to block the distal femur to prevent the cement from running down the entire length of the femoral medullary canal. Bone plugs are regularly used to accomplish this blockage to first help pressurize the proximal femur with wet bone cement. Cement pressurization is required in cemented hip surgery to ensure that the cement flows as far as possible into the cancellous bone and into the small crevasses of the intramedullary canal.

In addition, a bone plug keeps the bone cement in the site of the femoral hip stem. This prevents the need for large doses of cement to be used to fill the entire femoral canal. Filling the entire canal with cement would make revision surgery difficult.

Several bone plugs, such as that shown in U.S. Pat. No. 4,245,359 to Stuhmer and the Richards Buck Cement Restrictor show bone plugs with flanges. However, the Stuhmer plug allows too much bone cement to flow past the wide openings in each flange. The flanges of the Buck plug are not sufficiently deformable to allow easy insertion and proper sealing.

In the plug of the present invention, the flanges or fins deform backwards and fold over themselves during insertion to cause a friction fit with the inner walls of the canal. The trailing two fins are significantly larger in diameter than the leading fin. The trailing two fins have radial cuts in them to allow the flanges to fold over themselves causing a seal with the regular medullary canal. The cuts also prevent the flanges from buckling and allowing a channel for cement to escape past the plug. In addition, because the leading flange is of a smaller diameter than the rear flanges, it acts as a centering guide upon insertion.

These and other objects of the invention are accomplished by a plug for insertion into a bone medullary canal which has a hollow body with a longitudinal axis parallel to the long axis of the bone. The body includes at least three circumferential flanges extending outwardly therefrom in a direction perpendicular to the longitudinal axis of the body. At least one of the flanges has a varying thickness with the thickness being less at an outer circumferential edge than adjacent the body. At least one of the flanges has at least three narrow radially extending cuts or slits spaced around the circumferential extent thereof.

SUMMARY OF THE INVENTION

Accordingly, it is an object of the invention to prevent an axial displacement of a bone cement in a bone opening during insertion of an intramedullary stem of an endoprosthesis.

It is another object of the invention to permit an effective anchoring of an endoprosthesis stem within a bone.

Briefly, the invention provides a plug which can be inserted into an opening operatively formed in a bone canal in order to prevent axial displacement of a subsequently inserted bone cement when a stem of an endoprosthesis is inserted in the opening. The plug is formed with a plurality of coaxial flanges which are disposed in axially spaced relation along a longitudinal axis of the plug.

When used, the plug which preferably consists of a plastic used in conventional implants, for example, ultra high molecular weight polyethylene, is inserted into an opening which has been made in a bone such that the elastically deformable flanges of the plug are bent upwards towards the mouth of the opening. This deformation of the flanges clamps the plug against the bone wall. In this way, the flanges serve to extensively shut off the opening in the axial direction. The flanges can be adapted to the operative opening in the bone, for example, by keeping different sizes in stock. Thereupon, a bone cement of known type is introduced into the operation cavity.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
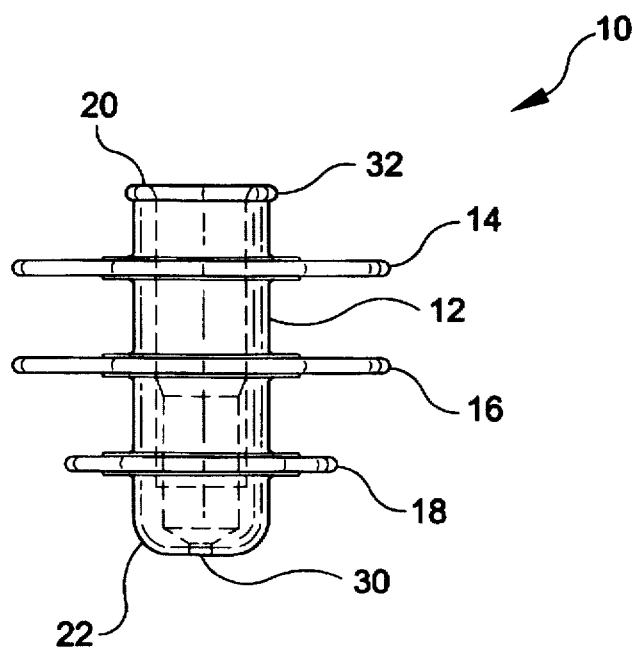
FIG. 1 is an elevation view of the plug of the present invention.
Figure 2:
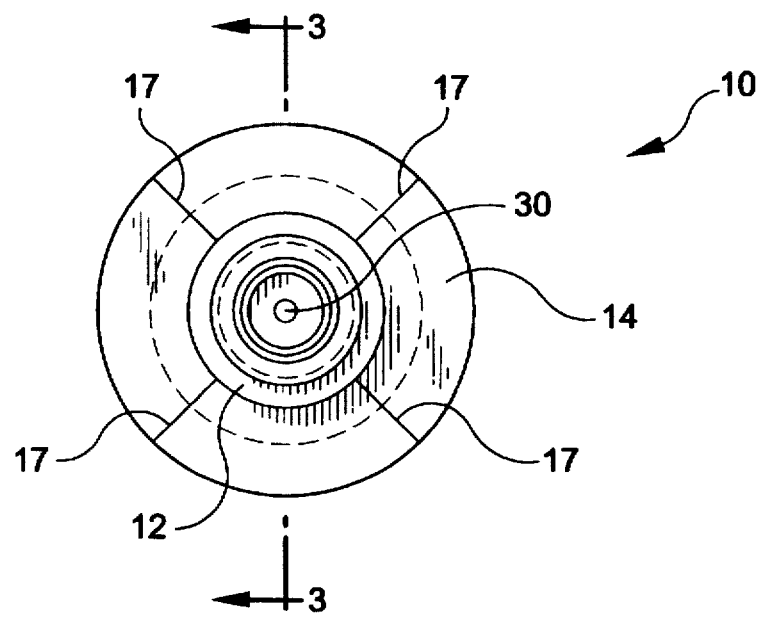
FIG. 2 is a top view of the plug of FIG. 1.
Figure 3:
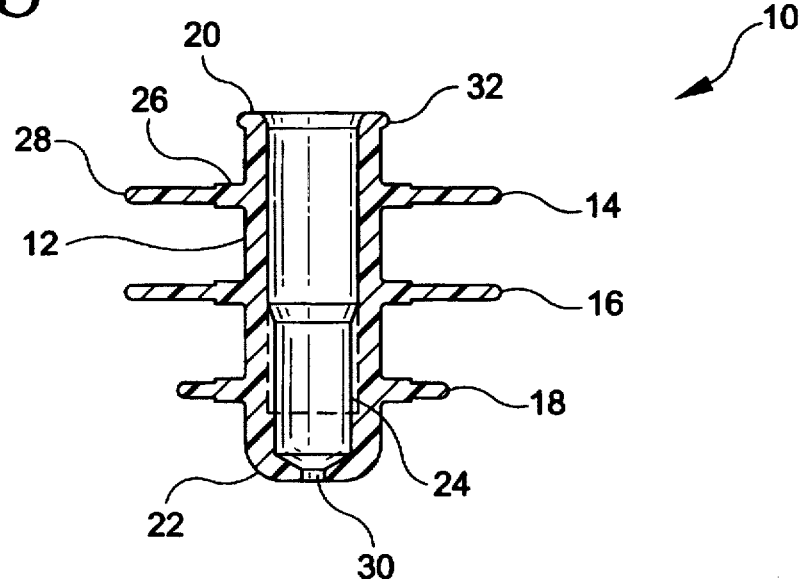
FIG. 3 is a cross-sectional view of the plug of FIG. 2 along lines 3—3.

Referring to the figures, there is shown the preferred bone plug generally denoted as 10, which includes a body 12 and three flanges 14, 16 and 18 extending radially outwardly therefrom.

The body portion 12 is generally cylindrical hollow body with an open first end 20 and a closed second end 22. The portion of the hollow body at the open first end 22 includes a threaded portion 24 adapted to receive an insertion tool (not shown) having a threaded tip.

In the preferred embodiment, the leading flange 18 is of a smaller diameter than the remaining flanges 14 and 16. The diameters of flanges 14 and 16 are, in the preferred embodiment, identical but could vary if desired.

Furthermore, additional flanges of varying diameters could be used. Furthermore, in the preferred embodiment, the flanges 14 and 16 have four narrow radial cuts or slits 17 formed by thin cutting instrument therein to allow the flanges to fold over themselves during insertion as to prevent buckling of the flanges. In the preferred embodiment there are at least three and preferably four slits 17 located at an angle with respect to one another, being 360° divided by the number of slits.

In addition, flanges 14, 16 and 18 can have a varying thickness which, in the preferred embodiment, comprises two steps with the thicker portion 26 adjacent the body and the thinner portion 28 adjacent the outer circumference of each of the larger flanges 14 and 16. The flanges, however, could be of constantly decreasing thickness as long as the external peripheral portion of each flange is thinner than the central portion 26. In the preferred embodiment, the thicker inner portion 26 of each flange is sized 0.5 mm in diameter smaller than the smallest recommend bone canal size for the plug. This ensures that the flanges 14, 16 are not overly flexible.

In use, several size bone plugs can be utilized to ensure a proper fit within a wide range of femurs. The plug 10 has a small hole 30 which extends from the threaded portion 24 of plug 10 through leading end 22 which acts to vent air or blood away from the surgical site and also prevents the presence of large air bubbles above the bone plug after the bone cement cures. In the preferred embodiment, the plug 10 has a 0.5 mm lip 32 around open end 20 thereof. This lip is used to help fix plug 10 to the hardened cement. This is advantageous since during revision surgery, the plug is likely to be removed with the cement column. The preferred plug 10 is fabricated from ultra high molecular weight polyethylene and may be injection molded.

Figure 4:
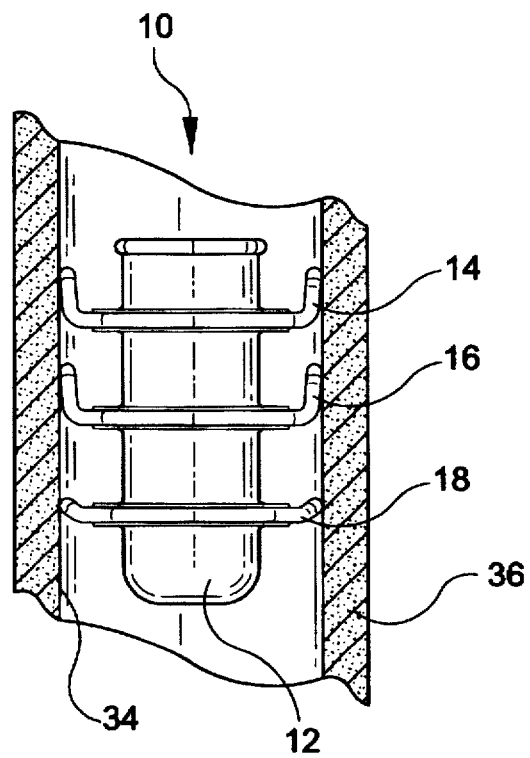
FIG. 4 shows the plug inserted in the medullary canal of a long bone.

Referring to FIG. 4 there is shown the plug after insertion into a medullary canal 34 surrounded by a long bone 36. As can be seen, the flanges 14,16 and 18 are deformed to provide an excellent grip with the wall of the canal. This friction fit with the wall not only prevents axial motion of the plug, but also prevents rotational movement prior to cementation. The slits or cuts enable the flanges to deform without buckling.

While several examples of the present invention have been described, it is obvious that many changes and modifications may be made thereunto, without departing from the spirit and scope of the invention.

We claim:

1. A plug for insertion into a bone having a medullary canal extending along an axis thereof to act as a cement barrier comprising:

a hollow body having a longitudinal axis parallel adapted to be positioned to said axis;

at least three circumferential flanges extending outwardly from said body in a direction generally perpendicular to said longitudinal axis, each of said flanges being of varying thickness with said thickness being less at an outer circumferential edge of said flanges having at least three radially extending narrow cuts formed by a thin cutting instrument spaced around the circumferential extent thereof, said cuts allowing sections of said flange to deform in an axial direction, each of said flanges having a first inner and second outer portion with two discrete thicknesses with said second portion being thinner and forming a step at the junction with said first portion.

2. The plug of claim 1 wherein said at least one flange has four cuts therein.

3. The plug of claim 2 wherein each cut is spaced 90° around the circumference of said flange.

4. The plug of claim 1 wherein said hollow body is open at one end and closed at a second end forming a U-shaped cavity.

5. The plug of claim 4 wherein said U-shaped cavity is at least partially threaded.

6. The plug of claim 4 wherein the flange adjacent said second end of said body has a smaller diameter than the remaining flanges.

7. The plug of claim 6 wherein at least one of said remaining flanges includes said cuts.

8. The plug of claim 4 wherein said closed end has a vent hole from said U-shaped cavity to the exterior of said body.

* * * * *